(12) United States Patent
Wrana et al.

(10) Patent No.: US 7,917,308 B2
(45) Date of Patent: Mar. 29, 2011

(54) PROCESS FOR DETERMINING A MOLECULAR WEIGHT DISTRIBUTION IN A POLYMER

(75) Inventors: Claus Wrana, Köln (DE); Jochen Kroll, Aachen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 619 days.

(21) Appl. No.: 11/982,912

(22) Filed: Nov. 6, 2007

(65) Prior Publication Data
US 2008/0162055 A1 Jul. 3, 2008

(30) Foreign Application Priority Data
Nov. 10, 2006 (DE) .......................... 10 2006 053 390

(51) Int. Cl.
*G01N 31/00* (2006.01)
*C08F 2/00* (2006.01)
(52) U.S. Cl. ........................................ 702/23; 526/60
(58) Field of Classification Search .................... 702/23; 526/60
See application file for complete search history.

(56) References Cited

U.S. PATENT DOCUMENTS
7,427,506 B2 * 9/2008 Garcia-Franco et al. ....... 436/85

OTHER PUBLICATIONS

Peirotti et al. [Latin American Applied Research, 33:185-194 (2003)].*
W. Thimm et al., "An Analytical relation between relaxation time spectrum and molecular weight Distribution", J. Rheol. 43 No. 6 (1999) 1663-1672.
Cole, R., Cole, H. J, Chem. Phys., 9:341, 1941 "Dispersion and Absorption in Dielectrics I. Alternating Current Characteristics".
Rouse, P.E., J. Chem. Phys., 21:1272, 1953 A Theory of the Linear Viscoelastic Properties of Dilute Solutions of Coiling Polymers.

* cited by examiner

*Primary Examiner* — William K Cheung
(74) *Attorney, Agent, or Firm* — Jennifer R. Seng

(57) ABSTRACT

The invention relates to a process for determining a molecular weight distribution in a polymer. When a polymer is prepared, chains of different length are formed. Correspondingly, a distribution of the molecular weights of the chains of a polymer arises.
It is an object of the invention to be able to determine the molecular weight distribution in an improved manner compared to the prior art.
The object of the invention is achieved by describing starting data $G^*(\omega)$ available in numerical form, i.e. the complex shear modulus measured as a function of frequency or the mastercurve constructed therefrom, are described by an analytical function. In this way, exact knowledge of the relaxation behaviour is available in improved form, in particular also in the case of prolonged relaxation times. This enables a valid determination of the relaxation time spectrum and hence a fundamentally more valid calculation of the molecular weight distribution.

8 Claims, 12 Drawing Sheets

PROCESS FOR DETERMINING A MOLECULAR WEIGHT DISTRIBUTION IN A POLYMER

FIELD OF THE INVENTION

The invention relates to a process for determining a molecular weight distribution in a polymer. When a polymer is prepared, chains of different length are formed. Correspondingly, a distribution of the molecular weights of the chains of a polymer arises.

BACKGROUND OF THE INVENTION

The prior art discloses various processes for determining a molecular weight distribution, for example under the name "GPC". In the GPC process, a polymer is dissolved and applied to a porous column. The faster the column is passed through, the higher the molecular weight. The speed with which the column is passed through is thus a measure of the molecular weight distribution.

This process has the disadvantage of only being able to analyze those polymers which are soluble. The sensitivity of the process also decreases with ever greater molecular weight.

In order to overcome the disadvantage regarding the sensitivity with increasing molecular weight, the prior art proposes calculating a molecular weight distribution on the basis of physical data. Such a process has become known, inter alia, from the publication "W. Thimm et al., An analytical relation between relaxation time spectrum and molecular weight distribution, J. Rheol. 43 No. 6 (1999) 1663-1672".

First, the complex shear modulus is measured as a function of frequency at different temperatures. For technical reasons, measurements are made at frequencies of $10^{-3}$ to $10^3$ Hz. Reduction of the frequency below $10^{-3}$ Hz causes the measurement time to grow greatly. For example, the measurement time at $10^{-3}$ Hz is 1 hours. For apparatus reasons, measurements above $10^3$ Hz are problematic, since intrinsic vibrations of the apparatus setup distort the result.

In order to be able to evaluate data over a relatively large frequency range irrespective of this problem, the fact that a measurement at relatively low temperatures can be converted by calculation to a measurement at relatively high frequencies is utilized. Such a conversion results in a so-called mastercurve which covers a relatively wide frequency spectrum. Two functions which characterize and reproduce the complex shear modulus with respect to frequency are then present in numerical form. One is the real part and the other the imaginary part. The real part is referred to as storage modulus and the imaginary part as loss modulus. The typical frequency range encompasses 14-20 decades, even though measurement has been effected only within the aforementioned frequency range.

According to the prior art, the so-called relaxation time spectrum is determined numerically therefrom. The numerical conversion of numerical starting data to a relaxation time spectrum is disadvantageously a so-called ill-posed problem. Errors in the starting data (measurements or values of the mastercurve) can be magnified by the conversion.

With the aid of the relaxation time spectrum and the generalized mixing rule, the distribution of the molecular weight m is determined numerically. The generalized mixing rule describes a relationship between the relaxation time spectrum h(m) and the molecular weight distribution ω(m). The relaxation time spectrum h(m) is available in numerical form. Therefore, this equation is solved numerically according to the prior art.

SUMMARY OF THE INVENTION

It is an object of the invention to be able to determine the molecular weight distribution in an improved manner compared to the prior art.

BRIEF DESCRIPTION OF THE DRAWINGS

In FIG. 4a, the five Cole-Cole functions are plotted separately. FIG. 4b shows the resulting process where $F_0=1$, $f_0=1$ and $\Delta=100$.

DETAILED DESCRIPTION OF THE INVENTION

Figure 1:
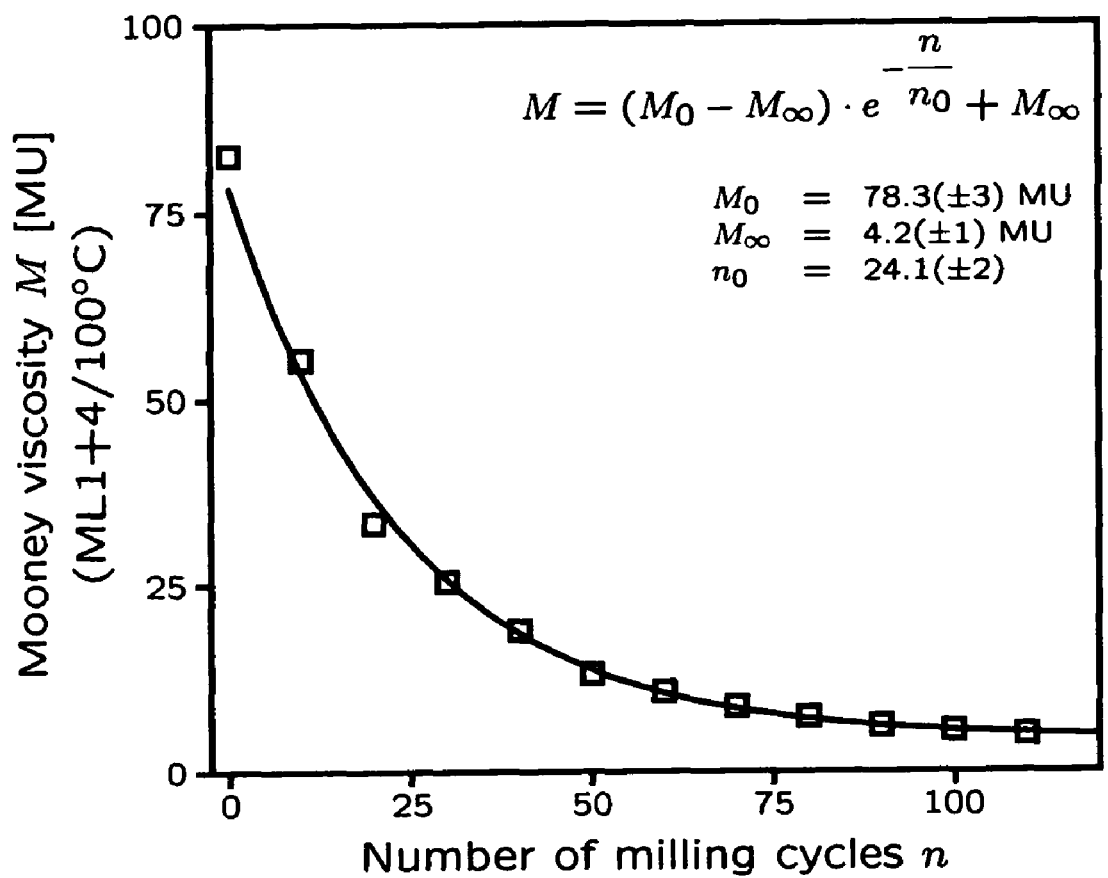
FIG. 1 shows the influence of the number of milling cycles n on the Mooney viscosity M [MU] (ML1+4/100° C.).

The object of the invention is achieved by describing starting data $G^*(\omega)$ available in numerical form, i.e. the complex shear modulus measured as a function of frequency or the mastercurve constructed therefrom, are described by an analytical function. In this way, exact knowledge of the relaxation behaviour is available in improved form, in particular also in the case of prolonged relaxation times. This enables a valid determination of the relaxation time spectrum and hence a fundamentally more valid calculation of the molecular weight distribution.

The molecular weight distribution can be calculated from the relaxation time spectrum and the generalized mixing rule. The following general mixing rule can be used for this calculation:

$$w(m) = \frac{1}{\beta}\left(\frac{\alpha}{G_0}\right)^{\frac{1}{\beta}} h(m) \left[\int_{lnm}^{\infty} h(m') d\ln m'\right]^{\frac{1}{\beta}-1}$$

where
$\omega(m)$: molecular weight distribution
$m, m'$: molecular weight
$\beta$: mixing parameter
$G_0$: plateau modulus The mixing parameter beta ($\beta$) is a fitting parameter. Practice has shown that $\beta$ equals 2 is a suitable value for finding the desired valid distribution function. $\beta$ may, though, for example, also be 1. This value is, though, less suitable.

First, a mastercurve is generally constructed from the complex shear modulus measured as a function of frequency. A relaxation time spectrum $h(\tau)$ is determined therefrom, preferably analytically.

In order to arrive at the relationship $h(m)$ from the relaxation time spectrum $h(\tau)$, one embodiment proceeds from the following relationship between relaxation time $\tau$ and the molar mass $m$ of an individual polymer chain, which, as experience has shown, correctly describes the desired relationship between a molecular weight of an individual polymer chain and the relaxation time $\tau$:

$$\tau = k \cdot m^{\alpha}.$$

The molecular weight m of an individual polymer chain can be calculated from the relaxation time $\tau$, by the relationship $\tau = k \cdot m^{\alpha}$. The constant k can be determined by calibration measurements. The value alpha ($\alpha$) can be obtained from measurements. For this purpose, polymers which have a known molecular weight distribution are available. Such polymers are known as calibration polymers. When the relaxation times are measured for such a known polymer, the desired constants can be determined. It has been found that, regularly, $\alpha = 3.4$.

It is not necessary to determine the constant k. This can in principle even be selected arbitrarily. However, the molecular weight distribution determined is then relative and not absolute.

A difficulty in the finding of an analytical equation for describing the starting data available in numerical form consists in describing the entire range of the relaxation for polymers. The common equations available do not cover the viscous flow of a polymer. This is true in particular also for the Cole-Cole function $$F_{cc}^*(\omega) = F_0 \cdot \frac{(i\omega\tau_0)^b}{1+(i\omega\tau_0)^b},$$

known from "Cole R., Cole H. J. Chem Phys., 9:341, 1941", which describes a relaxation process with the magnitude $F_0$, a mean relaxation time $\tau_0$ and a width parameter b.

In order to overcome this problem, one embodiment of the invention uses a sum of Cole-Cole functions with a width parameter $b=0.5$ in order to describe the starting data available in numerical form by an analytical function. It has been found that the sum should be formed from at least three Cole-Cole functions in order to arrive at a good result. The sum of five Cole-Cole functions, which is particularly preferable, is shown below.

$$F_{CCV}^*(f) = \sum_{v=0}^{4} F_{0_v} \frac{\sqrt{i\frac{f}{f_{0_v}}}}{1+\sqrt{i\frac{f}{f_{0_v}}}},$$

where $\omega = 2\pi f$ and $\tau_0 = 1/(2\pi f_0)$. Irrespective of the number of summed Cole-Cole functions, it has been found that it is particularly important to select the width parameter of 0.5 in order to arrive at a particularly good result.

The parameters $F_{0_v}$ and $f_{0_v}$ should advantageously be selected such that the sum of the Cole-Cole functions gives rise to the following: in the log-log plot, the real part must have the slope of 2 in the limiting case of small frequencies and the imaginary part must have the slope of 1 in the limiting case of small frequencies. The frequency-dependent behaviour of the storage modulus and of the loss modulus in the region of viscous flow is then described correctly.

In the case of a sum of five Cole-Cole functions, the following relationship accordingly exists between the aforementioned parameters $F_{0_v}$ and $f_{0_v}$:

$$f_{0_0} = f_0 \quad f_{0_1} = \frac{f_0}{\sqrt{\Delta}} \quad f_{0_2} = \frac{f_0}{\Delta} \quad f_{0_3} = \sqrt{\Delta} \cdot f_0 \quad f_{0_4} = \Delta \cdot f_0$$

$$F_{0_1} = F_{0_3} = F_0 \cdot \Delta^{\frac{1}{4}} \cdot \frac{(\Delta^2 - 1) \cdot (\Delta - 1)}{\Delta^{\frac{7}{2}} - \Delta^2 - \Delta^{\frac{3}{2}} + 1}$$

$$F_{0_2} = F_{0_4} = F_0 \cdot \Delta \cdot \frac{(\Delta - 1) \cdot \left(\Delta^{\frac{1}{2}} - 1\right)}{\Delta^{\frac{7}{2}} - \Delta^2 - \Delta^{\frac{3}{2}} + 1}.$$

When these three equations are satisfied, the frequency-dependent behaviour of the storage modulus and of the loss modulus is described correctly in the region of viscous flow.

$\Delta$ is a fitting parameter and describes the frequency separation of the various processes. To a certain degree, it is a width parameter as known from the Cole-Cole function. $F_0$ and $f_0$ are further fitting parameters. Overall, there thus remain three fitting parameters. The abovementioned limiting case of small frequencies f is pre-sent especially when $f \ll f_0/\Delta$.

The following advantages are offered by the process according to the invention:
It is possible to characterize insoluble polymers and polymers with very high molecular weights of more than 1 000 000 g/mol. Long-chain branching can be made better visible.

In order to calculate the molecular weight distribution exactly by means of the mixing rule, in one embodiment of the invention, the relaxation time spectrum is corrected by the contribution of the segment relaxations of the glass process. In the mastercurve, the glass transition becomes visible in that the storage modulus falls from the order of magnitude of 109 to 106. A precise distinction of glass and flow process is therefore possible. The glass process is preferably detected analytically by an independent function in the aforementioned manner and then removed from the calculation. In the case of determination of the glass process content in the relaxation spectrum, the procedure is thus in accordance with the invention.

To illustrate the advantages and possibilities of the present invention, analytically determined molecular weight distributions have been compared with the results determined by GPC measurements for three polymers NR, NBR and HNBR.

Pale crepe (NR) was ground for a particular number of milling cycles. Every ten cycles, a sample was taken. All milling experiments were performed at a temperature of 20° C. The diameter of the rollers used for the milling was 200 mm. The rotational frequency of the slower roller was adjusted to 20 revolutions/minute and to 24 revolutions/minute for the faster roller. The gap between the two rollers was 0.35 mm. A rough approximation of the maximum of the shear rate $\dot{\gamma}MAX$ can then be derived according to $$\dot{\gamma}_{MAX} = \frac{d\gamma_{MAX}}{dt} = \frac{dx}{dt} \cdot \frac{1}{g} = v \cdot \frac{1}{g} = \frac{r \cdot \Delta\omega}{g} \approx 120 \left[\frac{1}{s}\right],$$

the gap g between the mills and the difference in the rotational frequency of the rollers $\Delta\omega$ is known.

FIG. 1 shows the influence of the number of milling cycles n on the Mooney viscosity M [MU] (ML1+4/100° C.). The Mooney viscosity falls exponentially with increasing number of milling cycles. After 100 milling cycles, the Mooney viscosity remains constant at a value of about 4 Mooney grades. The table which follows summarizes the results determined for the Mooney and GPC measurements as a function of the milling cycles.

| Number of milling cycles | Mooney viscosity | $M_N$ [kg/mol] | $M_W$ [kg/mol] | $M_Z$ [kg/mol] | $M_P$ [kg/mol] | D |
|---|---|---|---|---|---|---|
| 0 | 83 | 311 | 892 | 1812 | 708 | 2.9 |
| 10 | 55 | 142 | 473 | 1178 | 452 | 3.3 |
| 20 | 33 | 110 | 302 | 550 | 357 | 2.8 |
| 30 | 25 | 104 | 263 | 465 | 292 | 2.5 |
| 40 | 19 | 96 | 229 | 401 | 236 | 2.4 |
| 50 | 13 | 91 | 201 | 348 | 200 | 2.2 |
| 60 | 11 | 77 | 172 | 304 | 157 | 2.2 |
| 70 | 9 | 73 | 159 | 276 | 147 | 2.2 |
| 80 | 7 | 76 | 155 | 263 | 152 | 2.1 |
| 90 | 6 | 73 | 146 | 246 | 141 | 2.0 |
| 100 | 5 | 68 | 141 | 240 | 134 | 2.1 |
| 110 | 5 | 65 | 133 | 226 | 124 | 2.0 |

$M_N$ is the number-average molar mass, $M_W$ is the weight-average molar mass, $M_Z$ is the Z-average molar mass, $M_P$ is the peak value of the molar mass distribution and D is the polydispersity. In this context: the equation $$M^{(\nu)} = \frac{\sum_{i=1}^{N} N_i \cdot M_i^{\nu}}{\sum_{i=1}^{N} N_i \cdot M_i^{\nu-1}}$$

describes a general relationship for the calculation of the average molar mass of a polymer consisting of N chains. $N_i$ is the number of chains with the molar mass $M_i$.

When $\nu=1$, this equation provides the definition of the number-average molar mass $M_N$. $\nu=2$ leads to the definition of the weight-average molar mass $M_W$. $\nu=3$ is known as the Z-average molar mass $M_Z$.

The polydispersity D is calculated according to $$D = \frac{M_W}{M_N} = N \cdot \frac{\sum_{i=1}^{N} N_i \cdot M_i^2}{\left(\sum_{i=1}^{N} N_i \cdot M_i\right)^2}.$$

The table which follows shows the results determined for the Mooney and GPC measurements including characterized NBR samples. The reduction in the molar mass was achieved by a metathesis reaction, which gives rise to a random reduction in the length of the polymer chains. The equilibrium condition of the metathesis reaction is thus characterized by a polydispersity of 2. After the metathesis reaction, all NBR samples were hydrogenated to HNBR (with about 2% residual double bonds).

| Sample | Mooney Viscosity | $M_N$ [kg/mol] | $M_W$ [kg/mol] | $M_Z$ [kg/mol] | $M_P$ [kg/mol] | D |
|---|---|---|---|---|---|---|
| NBR 1 | 28.8 | 82 | 262 | 875 | 112 | 3.2 |
| NBR 2 | 25.3 | 79 | 240 | 777 | 111 | 3.0 |
| NBR 3 | 21 | 75 | 201 | 551 | 108 | 2.7 |
| NBR 4 | 13.2 | 64 | 161 | 392 | 96 | 2.5 |
| NBR 5 | 8.1 | 56 | 135 | 307 | 87 | 2.4 |
| NBR 6 | 5.9 | 53 | 117 | 247 | 82 | 2.2 |
| NBR 7 | 2.7 | 44 | 89 | 164 | 72 | 2.0 |

The table which follows shows the results of the Mooney and GPC measurements. The NBR samples and the HNBR samples with an identical number (e.g. NBR 1 and HNBR 1) indicate the identical polymer before and after the hydrogenation process. Any difference in the properties can therefore be attributed to the hydrogenation process.

| Sample | Mooney Viscosity | $M_N$ [kg/mol] | $M_W$ [kg/mol] | $M_Z$ [kg/mol] | $M_P$ [kg/mol] | D |
|---|---|---|---|---|---|---|
| HNBR 1 | 76.8 | 98 | 278 | 764 | 131 | 2.9 |
| HNBR 2 | 66.9 | 88 | 260 | 711 | 127 | 2.9 |
| HNBR 3 | 58.6 | 87 | 238 | 627 | 125 | 2.7 |
| HNBR 4 | 40.2 | 81 | 193 | 457 | 112 | 2.4 |
| HNBR 5 | 29.6 | 67 | 159 | 342 | 103 | 2.4 |
| HNBR 6 | 22.9 | 63 | 143 | 299 | 98 | 2.3 |
| HNBR 7 | 11.6 | 52 | 107 | 201 | 83 | 2.1 |

The relaxation behaviour of all samples was characterized by mastercurves, which were constructed from frequency sweeps of the complex shear modulus $G^*(\omega)$ at different temperatures. The frequency sweeps of the complex modulus were measured in the temperature range of −80° C. to 100° C. with the Mettler STDA 816e in the range of 0.01 Hz to 1000 Hz using the "double sandwich sample holder". The Paar Physica MCR 300 rheometer was used for frequency-dependent measurements from 0.001 Hz to 100 Hz in the temperature range of 40° C. to 140° C. and for creep measurements for times which ranged from 0.1 s to 40 000 s at 100° C.

Creep measurements are normally used in order to characterize the time-dependent dynamic-mechanical behaviour for long times or small frequencies (t~1/f). The programme "NLREG" (Freiburg, Material Research Center. NLREG for nonlinear regularization, Version Rheology 2.0, 2001) was used to calculate the frequency-dependent modulus $G^*(\omega)$ from the time-dependent creep modulus G(t). This enables the characterization of the frequency-dependent behaviour at very small frequencies ($f<10^{-4}$ Hz).

Figure 2:
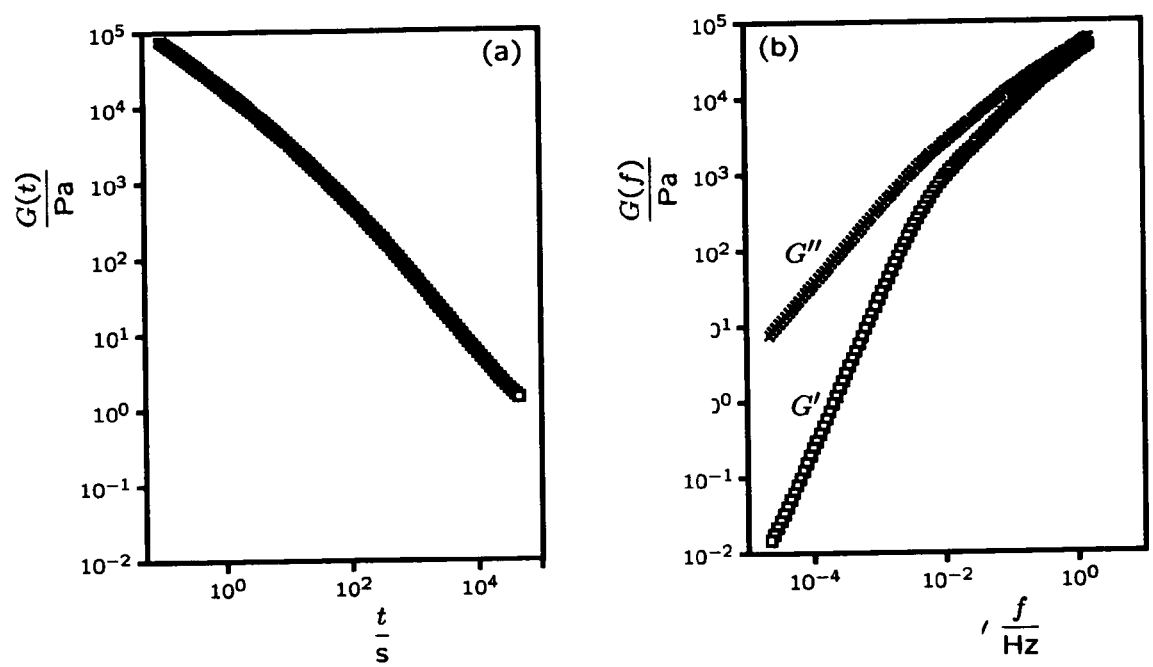
FIG. 2 shows the result of the calculation of the frequency-dependent behaviour from a creep experiment for natural rubber (pale crepe) which was milled for 60 cycles. A creep measurement (FIG. 2a) and a calculated frequency-dependent behaviour (FIG. 2b) are shown for NR (pale crepe) after 60 milling cycles.

FIG. 2 shows the result of the calculation of the frequency-dependent behaviour from a creep experiment for natural rubber (pale crepe) which was milled for 60 cycles. A creep measurement (FIG. 2a) and a calculated frequency-dependent behaviour (FIG. 2b) are shown for NR pale crepe) after 60 milling cycles.

Figure 3:
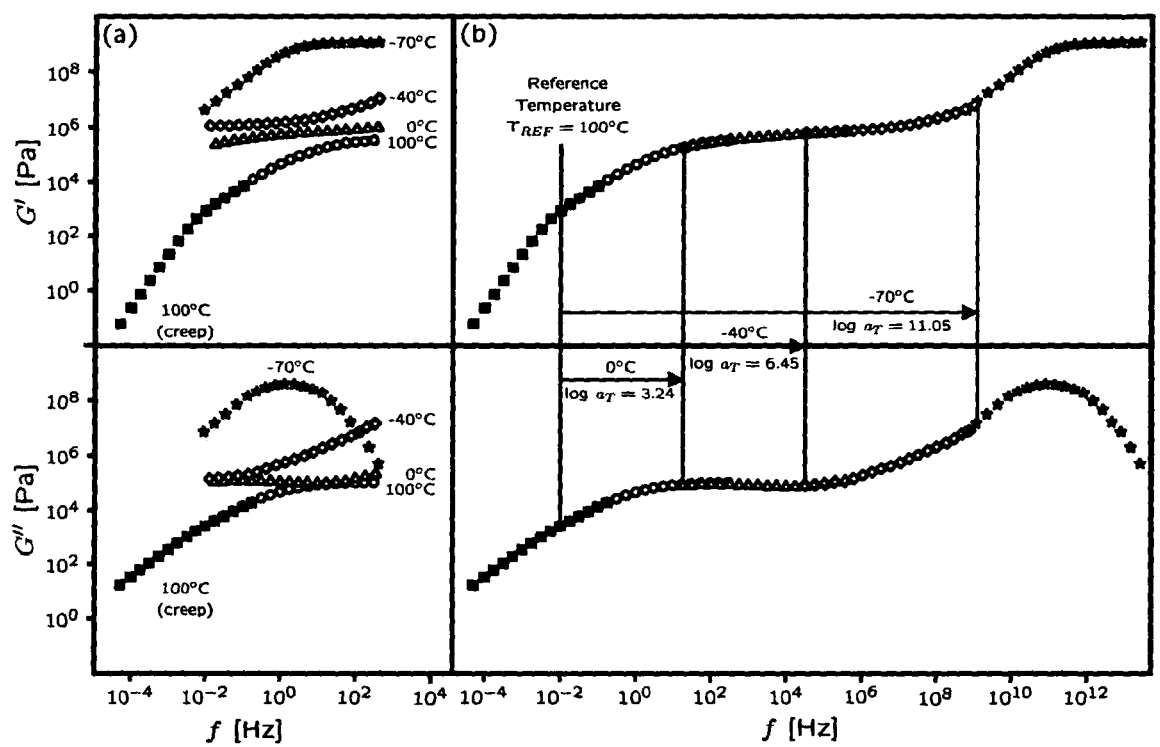
FIG. 3 shows the result of the construction of the master-curve for an NR after 60 milling cycles. Frequency-dependent measurements (FIG. 3a) and constructed mastercurve (FIG. 3b) are shown for NR (pale crepe) after 60 milling cycles.

Using the time-temperature equivalence principle, the calculated frequency-dependent data from creep experiments and the frequency-dependent measurements at different temperatures were combined to give a mastercurve which covers the dynamic-mechanical behaviour in a frequency range of nearly 20 decades. FIG. 3 shows the result of the construction of the mastercurve for an NR after 60 milling cycles. Frequency-dependent measurements (FIG. 3a) and constructed mastercurve (FIG. 3b) are shown for NR (pale crepe) after 60 milling cycles.

In order to evaluate the measurements analytically, a sum of five Cole-Cole functions with a constant b=0.5 was used:

$$F^*_{CCV}(f) = \sum_{v=0}^{4} F_{0_v} \frac{\sqrt{\iota \frac{f}{f_{0_v}}}}{1 + \sqrt{\iota \frac{f}{f_{0_v}}}}$$

The parameters $F_v$ and $f_{0_v}$ were selected such that the following boundary conditions were satisfied:

$$f_{0_0} = f_0 \quad f_{0_1} = \frac{f_0}{\sqrt{\Delta}} \quad f_{0_2} = \frac{f_0}{\Delta} \quad f_{0_3} = \sqrt{\Delta} \cdot f_0 \quad f_{0_4} = \Delta \cdot f_0$$

$$F_{0_1} = F_{0_3} = F_0 \cdot \Delta^{\frac{1}{4}} \cdot \frac{(\Delta^2 - 1) \cdot (\Delta - 1)}{\Delta^{\frac{7}{2}} - \Delta^2 - \Delta^{\frac{3}{2}} + 1}$$

$$F_{0_2} = F_{0_4} = F_0 \cdot \Delta \cdot \frac{(\Delta - 1) \cdot (\Delta^{\frac{1}{2}} - 1)}{\Delta^{\frac{7}{2}} - \Delta^2 - \Delta^{\frac{3}{2}} + 1}$$

Figure 4:
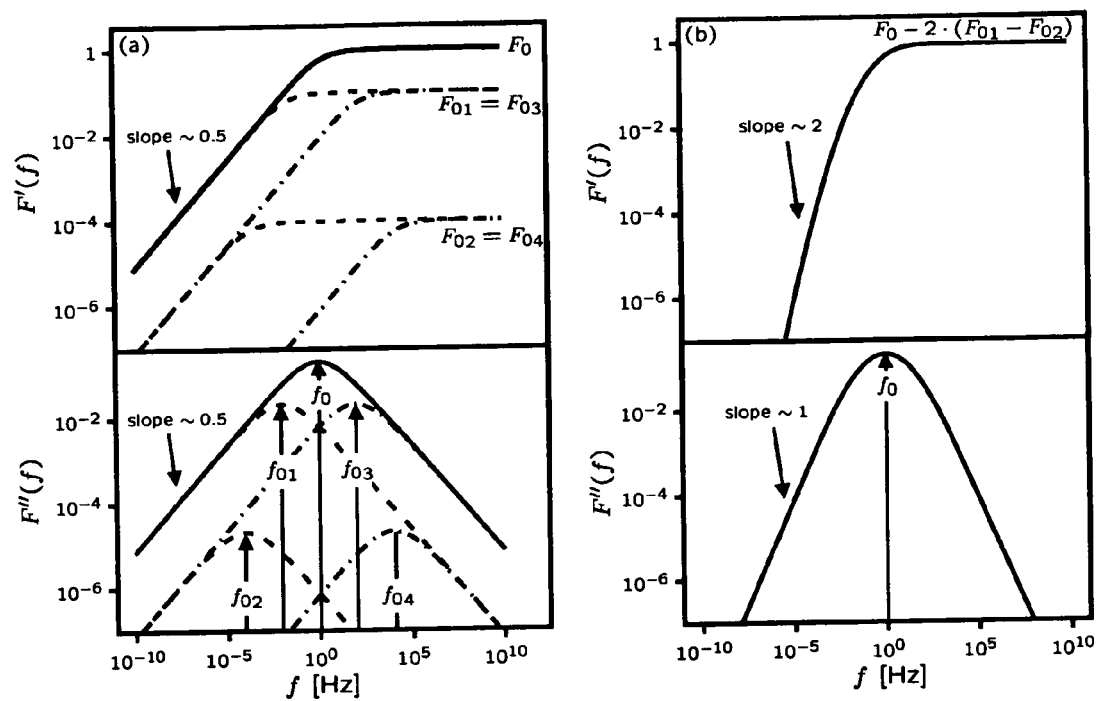
FIG. 4 shows an example of a relaxation process with a viscous ending.

This Cole-Cole function with a viscous ending $F^*_{CCV}(f)$ depends only on the parameters $F_0$, $f_0$ and $\Delta$. FIG. 4 shows an example of a relaxation process with a viscous ending. In FIG. 4a, the five Cole-Cole functions are plotted separately. FIG. 4b shows the resulting process where $F_0=1$, $f_0=1$ and $\Delta=100$.

Figure 5:
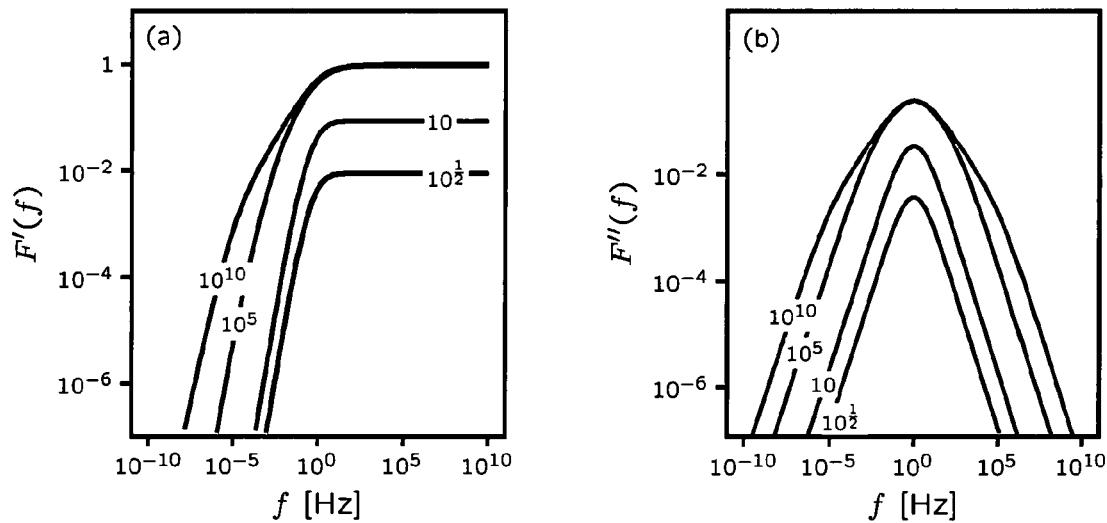
FIG. 5 illustrates the influence of the parameter $\Delta$ ($\Delta=10^{10}$, $10^5$, 1 and $10^{1/2}$) on the frequency-dependent behaviour.

FIG. 5 illustrates the influence of the parameter $\Delta$ ($\Delta=10^{10}$, $10^5$, 1 and $10^{1/2}$) on the frequency-dependent behaviour. The introduction of the ending condition gives rise to the following properties of the relaxation process:

Under the conditions of viscous flow, the storage and loss moduli are characterized by a frequency-dependent behaviour which reflects the behaviour of an ideal newtonian liquid.

The frequency at which the loss modulus reaches its maximum is identical to the relaxation frequency $f_0$.

The relaxation process with a viscous ending is characterized by three parameters: $F_0$, $f_0$ and $\Delta$. The width parameter b is constant (b=0.5).

The spectrum of the relaxation times is calculated analytically on the basis of the equations $$F_{cc}(\tau) = \frac{F_0}{\pi} \frac{\sin((1-b)\pi) \cdot \left(\frac{\tau}{\tau_0}\right)^b}{1 - 2\cos((1-b)\pi) \cdot \left(\frac{\tau}{\tau_0}\right)^b + \left(\frac{\tau}{\tau_0}\right)^{2b}}$$

and $$F^*_{CCV}(f) = \sum_{v=0}^{4} F_{0_v} \frac{\sqrt{\iota \frac{f}{f_{0_v}}}}{1 + \sqrt{\iota \frac{f}{f_{0_v}}}}.$$

The result is shown in FIG. 6a as a function of the parameter $\Delta$. FIG. 6b shows the result of the calculation of the distribution of the molar mass using the Cole-Cole equation $$w(m) = \frac{\alpha}{\beta}\left(\frac{1}{G_0}\right)^{\frac{1}{\beta}} \frac{\sum_i \frac{F_{0_i}}{\pi} \frac{\sin((1-b_i)\pi) \cdot \left(\frac{m}{m_{0_i}}\right)^{b_i \cdot \alpha}}{1 - 2\cos((1-b_i)\pi) \cdot \left(\frac{m}{m_{0_i}}\right)^{b_i \cdot \alpha} + \left(\frac{m}{m_{0_i}}\right)^{2b_i \cdot \alpha}}}{\left(\sum_i \frac{F_{0_i}}{\pi b_i} \cdot \left\{\frac{b_i \pi}{2} - \arctan\left[\frac{1 - \left(\frac{m_{0_i}}{m}\right)^{b_i \cdot \alpha}}{1 + \left(\frac{m_{0_i}}{m}\right)^{b_i \cdot \alpha}} \cdot \tan\frac{b_i \pi}{2}\right]\right\}\right)^{1-\frac{1}{\beta}}}$$

for the above relaxation processes.

Figure 6:
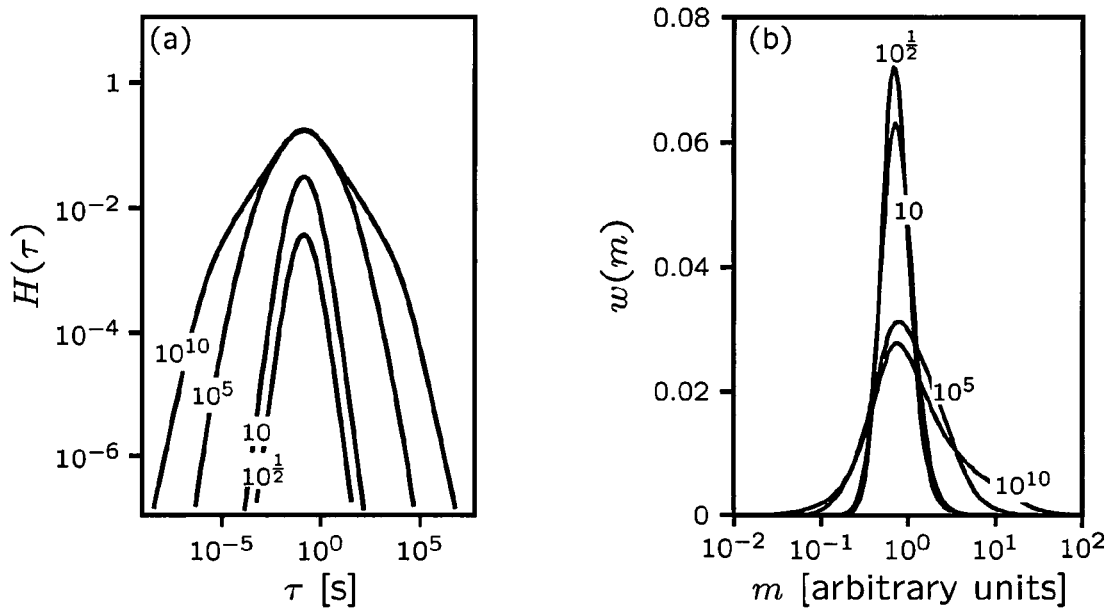
FIG. 6 illustrates the influence of the ending ratio ($\Delta=10^{10}$, $10^5$, 1 and $10^{1/2}$) on the spectrum of the relaxation times.

In the section which follows, the calculation of the molar mass distribution by the process according to the invention, referred to hereinafter as DMA, is demonstrated for NR after 60 milling cycles. FIG. 6 illustrates the influence of the ending ratio ($\Delta=10^{10}$, $10^5$, 1 and $10^{1/2}$) on the spectrum of the relaxation times.

Figure 7:
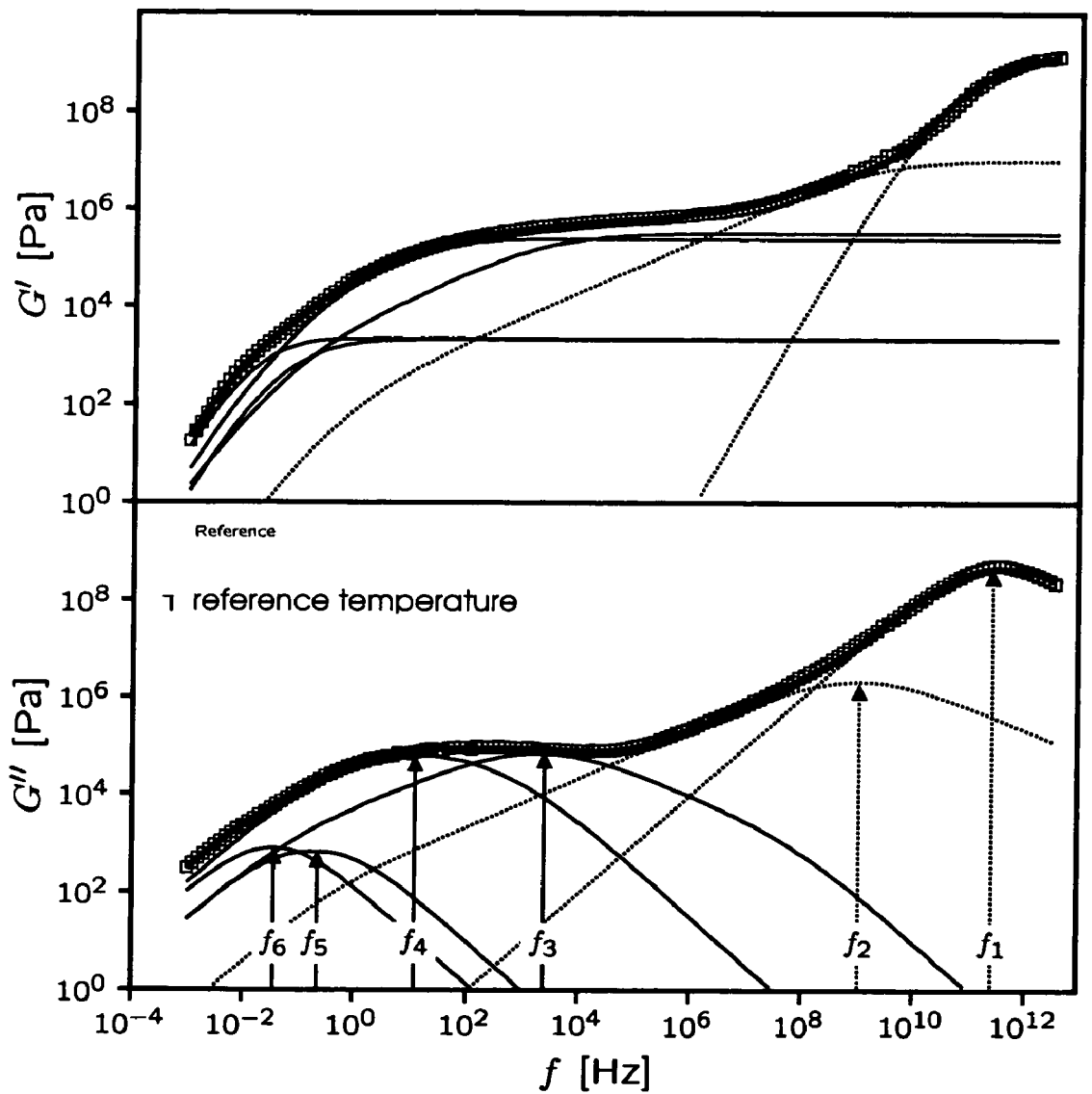
FIG. 7 shows the result of fitting by the least squares method of the relaxation functions to the frequency-dependent values of the storage and loss moduli.

The mastercurve (see FIG. 3a) was described analytically by a sum of six relaxation functions with viscous ending. FIG. 7 shows the result of fitting by the least squares method of the relaxation functions to the frequency-dependent values of the storage and loss moduli.

Fitting with the least squares method was implemented as an Excel macro and allows fitting of up to 8 relaxation functions with a viscous ending to the values of the storage and loss moduli of a given mastercurve. The best fitting condition is shown in the following equation.

$$\sum_{i=1}^{N}\left[\left(\log G'(f_i) - \log \sum_v F'_{CCV_v}(f_i)\right)^2 + \left(\log G''(f_i) - \log \sum_v F''_{CCV_v}(f_i)\right)^2\right] \stackrel{!}{=} \text{MIN}$$

Owing to the great deviation in the storage and loss moduli, a logarithmic scale of the data and function values was selected. This also restricts the dominance of the conditions of the glass transition over the entire frequency range.

Fitting of the relaxation functions to the mastercurve (see FIG. 7) gives rise to the parameters of the relaxation functions. FIG. 7 shows an analytical description of the master-curve of NR (pale crepe) after 60 milling cycles with relaxation functions having a viscous ending.

Figure 8:
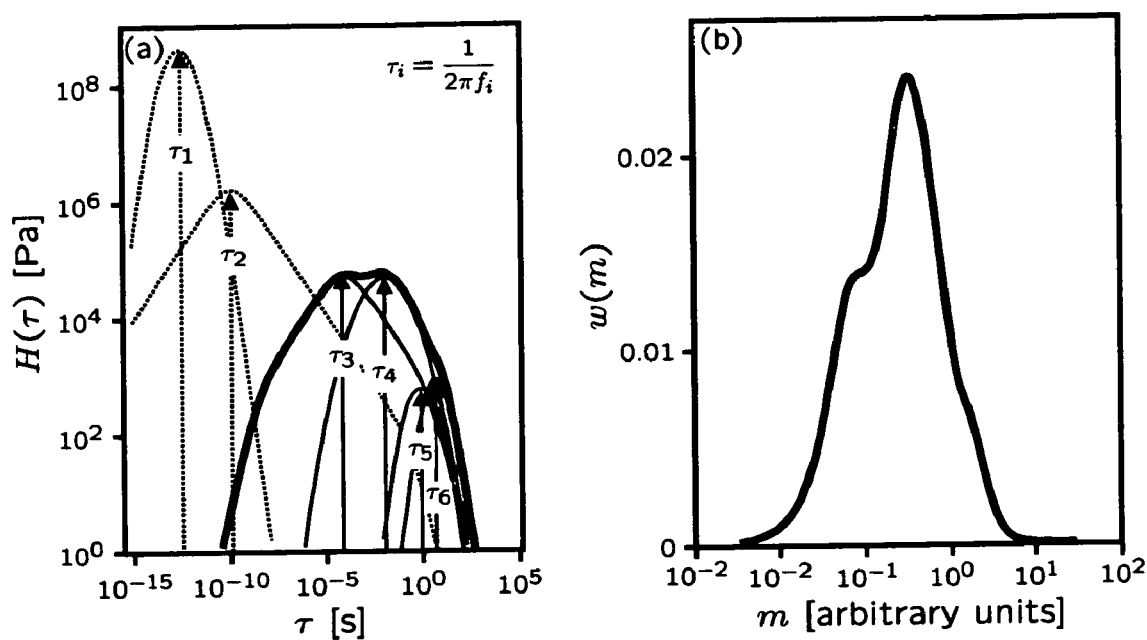
FIG. 8 shows the spectrum of relaxation times which has been calculated from the parameters of the relaxation times.

Since the spectrum of relaxation times is described by a sum of relaxation functions with a viscous ending (see equation $$F_{cc}(\tau) = \frac{F_0}{\pi} \left( \frac{\sin((1-b)\pi) \cdot \left(\frac{\tau}{\tau_0}\right)^b}{1 - 2\cos((1-b)\pi) \cdot \left(\frac{\tau}{\tau_0}\right)^b + \left(\frac{\tau}{\tau_0}\right)^{2b}} \right),$$

a numerical calculation of the spectrum of relaxation times is no longer necessary. FIG. 8 shows the spectrum of relaxation times which has been calculated from the parameters of the relaxation times.

In the calculation of the molar mass distribution from the spectrum of relaxation times, the following assumption was made. Thimm et al. [Thimm W., Friedrich C., Honerkamp J., J. Rheol., 6:43, 1999] noticed that only the time of a repetition of a chain in a tube correlates directly with the chain length. Shorter relaxation times are caused by the relaxation of chain segments (the so-called Rouse modes). The distribution of the chain length is therefore calculated advantageously by subtracting the Rouse modes from the spectrum of the relaxation times.

Since the theoretical derivation of the contribution of the Rouse modes [Rouse, P. E., J. Chem. Phys., 21:1272, 1953] to the spectrum of the relaxation times does not correlate well with the experimental results (especially under the conditions of the glass transition), an empirical approach was chosen and the relaxation of chain segments was approximated by two relaxation functions with a viscous ending (see dotted lines in FIG. 8a). After the substraction of the two relaxation functions, the distribution of the molar mass was calculated analytically from the spectrum of the remaining relaxation functions (see FIG. 8b). FIG. 8 shows a spectrum of the relaxation time and distribution of the molar mass of NR (pale crepe) after 60 milling cycles.

Figure 9:
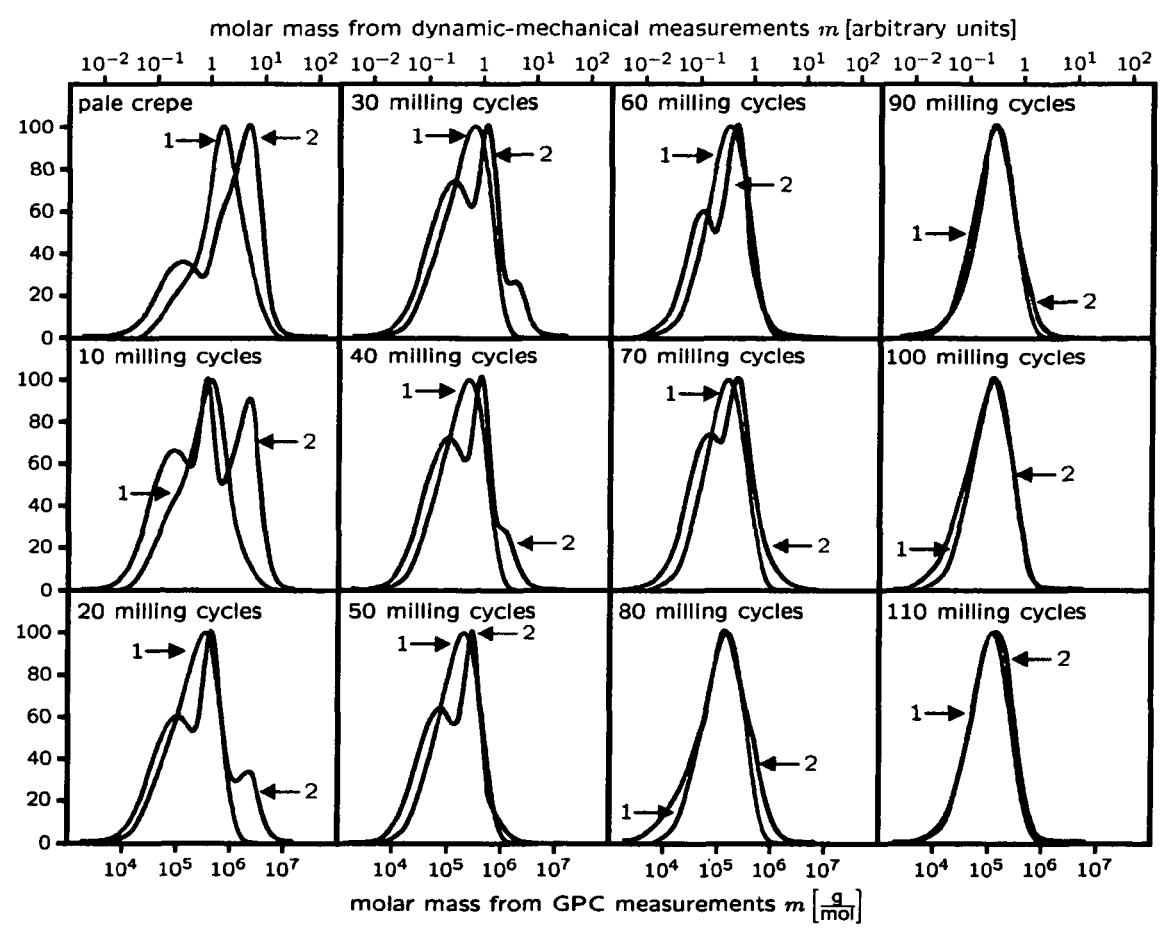
FIG. 9 shows the result of the GPC (curves 1) and of the DMA (curves 2) of NR as a function of the number of milling cycles according to the first table.

FIG. 9 shows the result of the GPC (curves 1) and of the DMA (curves 2) of NR as a function of the number of milling cycles according to the first table. Since the dynamic-mechanical data, i.e. the DMA data, have not been calibrated, the values for the molar mass on the upper axes are only relative numbers.

The comparison of the molar mass distribution from GPC and DMA shows a good correlation for the NR samples which have been milled for more than 80 cycles, and allows a rough calibration of the dynamic-mechanical data. For relatively small numbers of mixing cycles, the results of the two processes differ significantly.

The results of the dynamic-mechanical analysis can be summarized as follows.

The unmilled NR is characterized by a bimodal distribution with the molar masses $M_1 \approx 10^5$ g/mol and $M_2 \approx 2 \times 10^6$ g/mol.

After 10 milling cycles, a third peak ($M_3 = 4 \times 10^5$ g/mol) appears in the distribution of the molar mass. The molar mass of this peak remains unchanged until 50 milling cycles have been performed.

The intensity of the peak with the highest molar mass $M_2 \approx 2 \times 10^6$ g/mol decreases with a growing number of milling cycles, and disappears after about 50 mixing cycles.

After about 50 milling cycles, the molar mass distribution is again bimodal with $M_1 \approx 7 \times 10^4$ g/mol and $M_3 = 3 \times 10^5$ g/mol. A further growth in the number of milling cycles reduces the intensity of the fraction with the larger molar mass $M_3$. At about 80 milling cycles, the distribution of the molar mass is close to a monomodal distribution function with a maximum of about $M_P \approx 1.4 \times 10^5$ g/mol.

A further increase in the number of milling cycles gives rise only to a small reduction in the peak value (from about $1.4 \times 10^5$ g/mol after 80 milling cycles down to about $1.0 \times 10^5$ g/mol after 110 milling cycles).

The results of the dynamic-mechanical analysis (DMA) can be interpreted when two assumptions are made.
1. The NR analyzed is a blend of at least three fractions with different molar masses, the fraction with the highest molar mass being dominant.
2. Shorter chains are more stable than longer chains.

When the longer chains are broken up first, the fraction with the greatest molar mass is at first influenced the most by the milling process.

After 10 milling cycles, the fraction with the highest molar mass no longer dominates the mixture. After about 50 milling cycles, the longest chains have nearly disappeared. The distribution of the molar mass is now dominated by the fraction with the second largest molar mass. After 80 milling cycles, most chains have been broken up, and the molar mass distribution is dominated by the fraction with the lowest molar mass.

If the stability of a chain depends upon its length, the reduction in the molar mass is restricted to a critical value. At the critical length, the applied mechanical field, which is proportional to the shear rate (see equation $$\dot{\gamma}_{MAX} = \frac{d\gamma_{MAX}}{dt} = \frac{dx}{dt} \cdot \frac{1}{g} = v \cdot \frac{1}{g} = \frac{r \cdot \Delta\omega}{g} \approx 120 \left[\frac{1}{s}\right] ,$$

is too small to break up the chains. This indicates an essentially constant molar mass distribution after a particular number of milling cycles. In the experiment performed, the maximum value of the molar mass is about $1 \times 10^5$ g/mol after 90 milling cycles, and remains constant after further milling.

The comparison of the results from the DMA with the results of the GPC analysis shows significant differences for the first milling cycles. A rise in the number of milling cycles leads to comparability of the two processes.

The difference in the results of the two processes can be explained when it is borne in mind that the fraction with the large molar mass is insoluble, and is therefore not detected by the GPC process. After a certain number of milling cycles, the insoluble fraction with the greatest molar mass has been removed. The results of the GPC measurement are therefore similar to the results determined by the invention (DMA). A quantitative comparison of the two processes shows that the use of the GPC process is problematic when the molar mass of the chains in the polymer exceeds $1 \times 10^6$ g/mol. Judging by the results, chains with a greater molar mass are not detected by the GPC process used.

Figure 10:
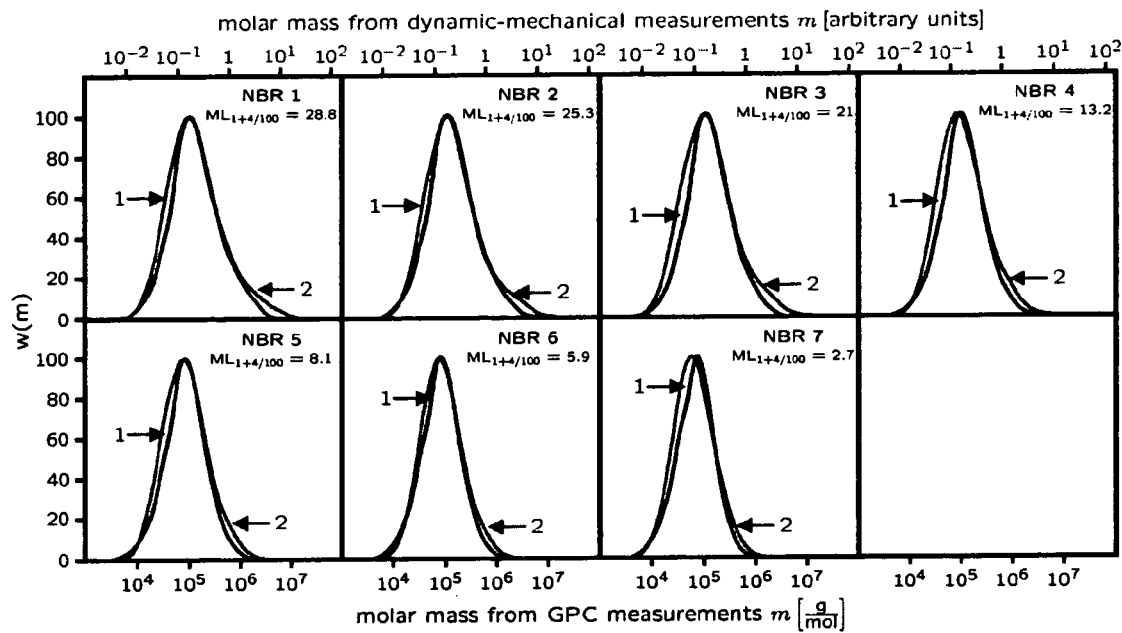
FIG. 10 shows a characterization of the molar mass of NBR with GPC (curves 1) and DMA (curves 2).
Figure 11:
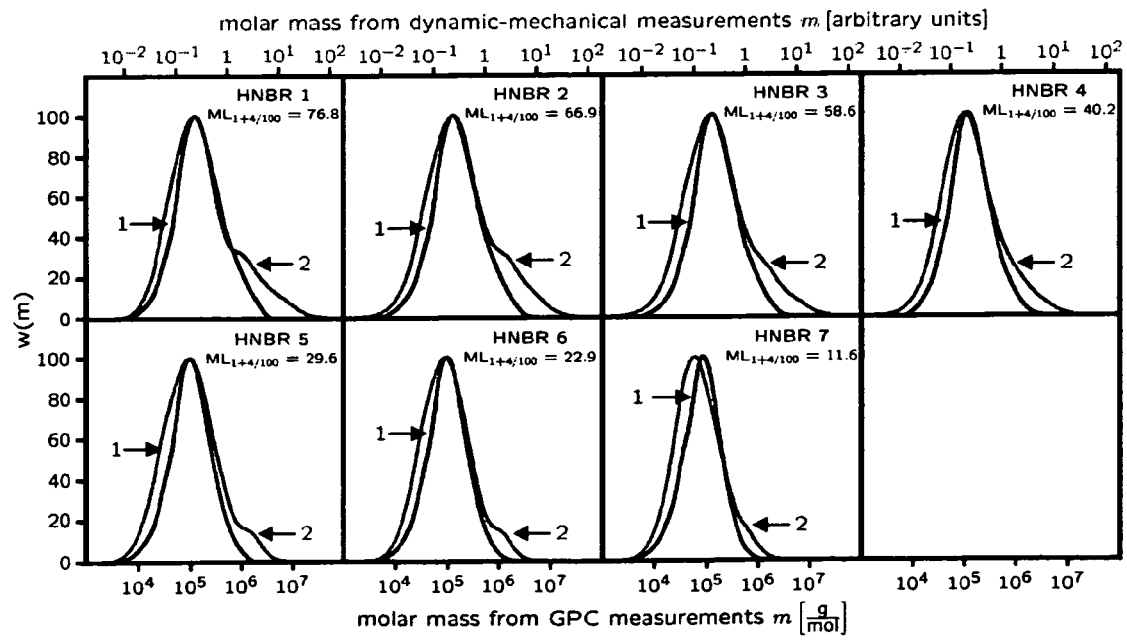
FIG. 11 shows the same comparison is performed for the HNBR samples. Characterization of the molar mass distribution of HNBR with GPC (curves 1) and DMA (curves 2).

The results of the determination of the molar mass distribution of NBR and HNBR samples are shown in FIGS. 10 and 11. The curves 1 relate to the results of the GPC measurements and the curves 2 to the results of the dynamic-mechanical experiments (DMA), i.e. to the results obtained by the invention. A quantitative comparison of the two processes is in turn not possible, since the results of the dynamic-mechanical measurements (DMA) have not been calibrated independently. The values of the molar mass from the DMA on the upper axes are thus again relative numbers.

A comparison of the NBR results shows a good qualitative agreement between the GPC process and the DMA process. Significant differences occur only at relatively high molar masses. The difference between the results of the two processes can again be explained only by insoluble polymer fractions. These insoluble fractions, which cannot be detected by the GPC process, might be caused either by chains with a very high molar mass or by chains with a branched structure.

The theory behind both processes is based on the assumption that all chains in the polymer are linear. When branching occurs, the results of the GPC and of the DMA are influenced in different ways.

The principle of the GPC process is the dependence of the size of a polymer chain (i.e. of the radius of gyration) on the diffusion within porous materials. A smaller chain requires a longer time to diffuse through a porous material than a longer chain. Since branched structures always have a smaller radius of gyration than linear chains of comparable molar mass, the branched structure requires longer for the diffusion process. The molar mass of a branched structure is therefore underestimated by the GPC measurement.

FIG. 10 shows a characterization of the molar mass of NBR with GPC (curves 1) and DMA (curves 2). In the case of DMA, it should be borne in mind: since the molar mass is related to the relaxation time of the entire chain and the relaxation of a branched chain is slower than the relaxation of a linear chain with comparable molar mass, the molar mass can be overestimated by DMA. A comparison of the molar mass distribution from GPC and from DMA in the region of large molar masses can therefore be used as an indication for the presence of branching of long chains.

When the molar mass distributions from GPC and DMA are compared for the NBR samples in the region of relatively large molar masses (see FIG. 10), the DMA values are slightly higher than the values of the GPC measurements. This indicates the existence of a small contribution of branched structures of long chains.

When the same comparison is performed for the HNBR samples [see FIG. 11—Characterization of the molar mass distribution of HNBR with GPC (curves 1) and DMA (curves 2)], the results from the DMA show a significantly higher fraction of chains with higher molar masses than the results from the GPC measurements. One possible explanation would be additional branching of the polymer chains during the hydrogenation.

An alternative explanation is based on the influence of the flexibility of the polymer chains on their relaxation behaviour. The increased flexibility of a hydrogenated polymer chain gives rise to a greater relaxation time which causes an increased volume viscosity. Since the influence of the chain flexibility on the viscosity is greater for branched chains of long chains, the contribution of branched chains to the molar mass distribution would be increased when the branched chains gain more flexibility.

On the basis of the present results, a quantitative validation of a possible branching reaction during the hydrogenation reaction is not possible. This would necessitate a repetition of the experiments with a series of NBR samples with different viscosity and complete linear chain structure.

When no side reaction occurs during the hydrogenation, the hydrogenation would influence only the flexibility of the polymer chains. Since the influence of the chain flexibility depends on the viscosity of the chain structure, and the hydrogenation of a branched structure gives rise to a significantly higher viscosity than the hydrogenation of a linear chain structure, the differences between the NBR results and the HNBR results might be a qualitative indication for the existence of a fraction of branched polymer chains in the NBR.

A frequently discussed effect is the so-called "Mooney jump", which describes the fact that the Mooney viscosity rises significantly after the hydrogenation of the double bonds of the NBR.

Figure 12:
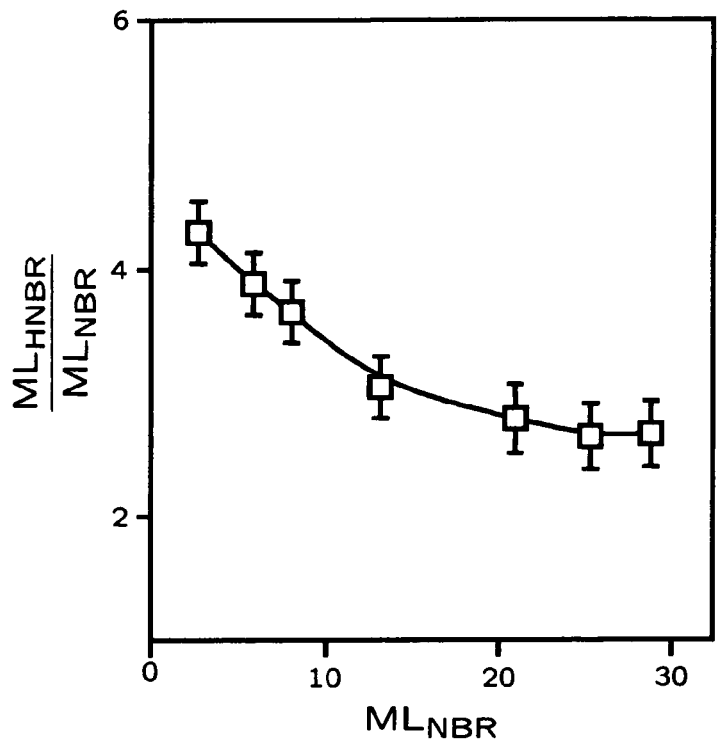
FIG. 12 shows where the Mooney viscosities $ML_{1+4/100}$° C. (referred to hereinafter as ML) of the NBR are plotted against the ratio of the ML of the HNBR and NBR.

This is shown clearly in FIG. 12, where the Mooney viscosities $ML_{1+4/100° C.}$ (referred to hereinafter as ML) of the NBR are plotted against the ratio of the ML of the HNBR and NBR. The ML of the HNBR is not only greater than that of the NBR from which it has been derived, but the ratio of the Mooney viscosity reaches the greatest values when the Mooney viscosity of the NBR is low. The higher the Mooney viscosity of the NBR, the smaller the effect of the "Mooney jump".

To date, it is unclear which mechanism is responsible for the "Mooney jump" and its dependency on the Mooney viscosity of the NBR.

A possible explanation for the higher Mooney viscosities of the HNBR compared to the NBR is the existence of chemical side reactions during the hydrogenation process, which generate a higher amount of high molecular weight and/or branched chains.

An alternative explanation is based on the flexiblity of the NBR polymer chains, which rises owing to the hydrogenation. The higher flexibility of the hydrogenated polymer chains would give rise to a higher amount of entanglement. Since a larger number of entanglements results in higher viscosity, it can be concluded that an increased flexibility of the main chain is always accompanied by a higher volume viscosity.

Figure 13:
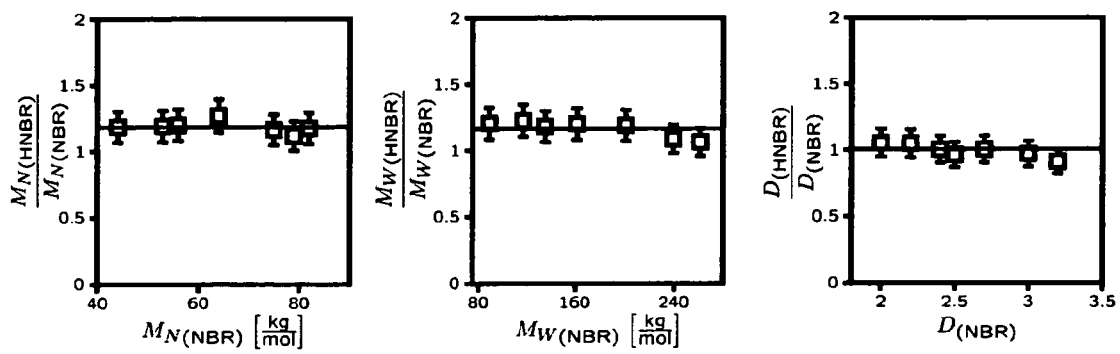
FIG. 13 illustrates a comparison of the average values of the molar masses of NBR and HNBR, measured by GPC.

A comparison of the GPC results of the NBR and HNBR polymers shows that the number-average and weight-average molar masses of the HNBR samples are only about 10% to 20% higher than the average values of the corresponding NBR samples (see FIG. 13—Comparison of the average values of the molar masses of NBR and HNBR, measured by GPC). In addition, the GPC results do not show any dependence of the ratio of the molar masses on the molar mass of the NBR.

Since GPC is not capable of detecting very high molecular weight and/or long-chain-branched fractions, the results of the DMA can be utilized in order to elucidate the mechanism behind the Mooney jump.

Figure 14:
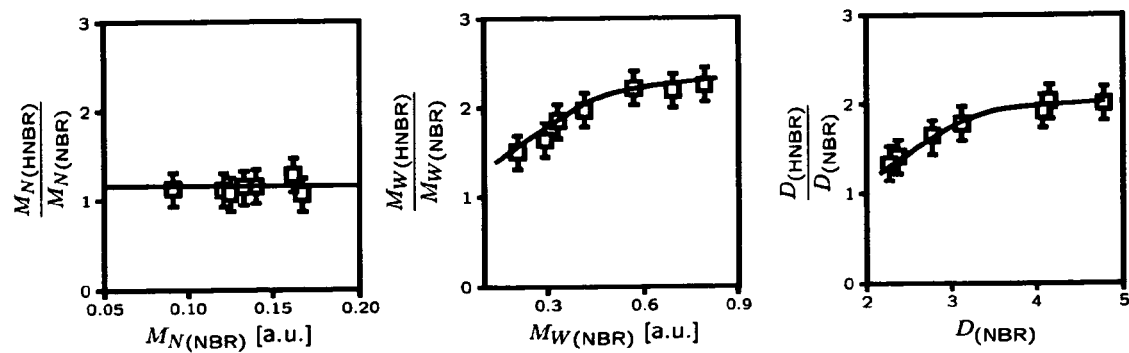
FIG. 14 demonstrates a comparison of the dynamic-mechanical results of the NBR and HNBR polymers showing that the number average molar mass of ther HNBR is about 10% to 20% higher than the average values of the corresponding NBR samples.

A comparison of the dynamic-mechanical results (see FIG. 14) of the NBR and HNBR polymers shows that the number-average molar mass of the HNBR is about 10% to 20% higher than the average values of the corresponding NBR samples. The result is similar to the results of the GPC measurements.

The characterization of the weight-average molar masses gives opposing results for the GPC and DMA measurement. While the GPC results detect a constant ratio between the weight-average molar masses of HNBR and NBR, DMA detects a significant influence of the molar mass. The ratio of the weight-average molar mass of HNBR and NBR rises with the molar mass and attains a plateau value for the highest molar masses (see the middle and the right-hand diagram in FIG. 14—comparison of the average values of the molar masses of NBR and HNBR, measured with dynamic-mechanical analysis).

The results of the GPC and of the dynamic-mechanical analysis (DMA) of NBR and HNBR indicate two possible mechanisms as a reason for the Mooney jump.

The higher flexibility of the hydrogenated NBR-chains
This gives rise to an increased radius of gyration and a higher viscosity. Since the molar mass is calculated from the radius of gyration (GPC process) or from the volume viscosity (DMA), a rise in the flexibility of the hydrogenated chain would cause a constant rise in the molar mass. The experimental confirmation is given by the fact that the ratio of the number-average molar mass appears to be independent of the molar mass for both processes.

The existence of long branched chains

When the degree of branching is increased, the radius of gyration shrinks, and the viscosity increases. The GPC process therefore underestimates the molar mass of a branched structure, while the dynamic-mechanical analysis gives rise to the opposite effect.

Since the hydrogenation gives rise to a higher chain flexibility, the influence of the branching on the radius of gyration and the viscosity is greater than in the case of a more flexible chain.

Differences in the results of the GPC process and of the dynamic-mechanical process at relatively high molar masses might therefore be attributed to a fraction of branched polymer chains. This can be seen in the diagrams of the molar mass distribution (see FIG. 10 and FIG. 11) and in the comparison of the influence of the molar mass on the weight-average molar mass (compare FIG. 13 and FIG. 14).

With the above explanations, the Mooney jump can be attributed to the increased flexibility of the hydrogenated polymer chain.

The decrease in the ratio of the Mooney viscosities at relatively high Mooney viscosities (see FIG. 12) cannot be explained by an increased flexibility of the polymer chain. The increased flexibility would give rise to a constant viscosity ratio of HNBR and NBR for linear polymer chains and an increased viscosity ratio for branched or partly branched polymers.

Figure 15:
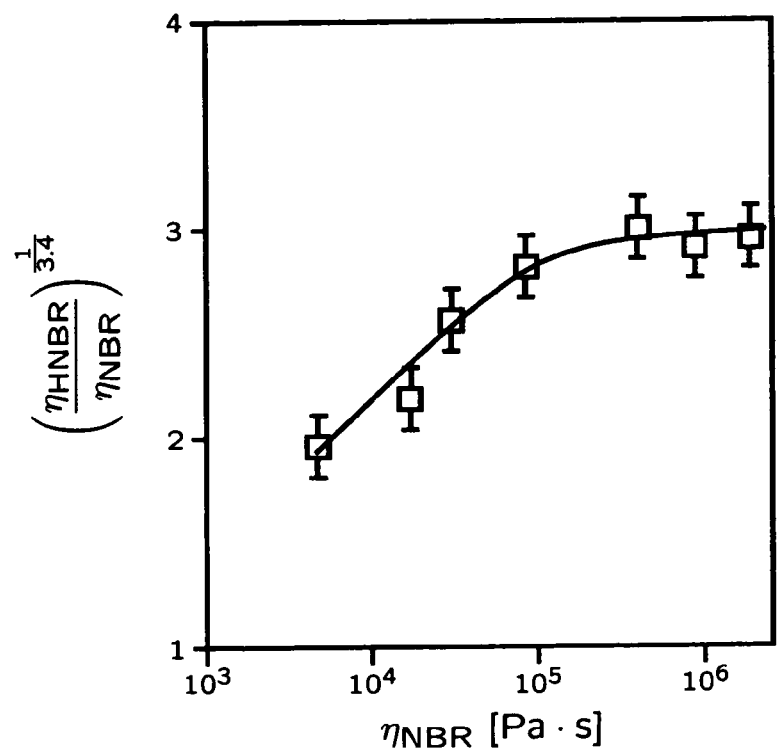
FIG. 15 shows viscosities of NBR and HNBR and plotted as a function of the viscosity of the NBR.

Since the conditions of the Mooney measurements are not really well defined, the ratio of the shear viscosities was additionally calculated from the dynamic-mechanical measurements with the aid of the equation $$\eta = \lim_{\omega \to 0} \frac{|G^*(\omega)|}{\omega}$$

and plotted as a function of the viscosity of the NBR (see FIG. 15, which shows viscosities of NBR and HNBR). The result is completely different from the result of the Mooney measurements. A rise in the viscosity of the NBR increases the ratio between the viscosity of the HNBR and of the NBR. At the highest viscosities of the NBR, the ratio reaches a constant plateau.

The explanation of the contrary results is based again on the influence of the chain structure and its flexibility on the viscosity.

For entangled linear polymers, a rise in the shear rate gives rise to a decrease in the volume viscosity. A branched polymer with a comparable molar mass is characterized by a higher viscosity at low shear rates and by a greater reduction in the viscosity at increased shear rates.

Figure 16:
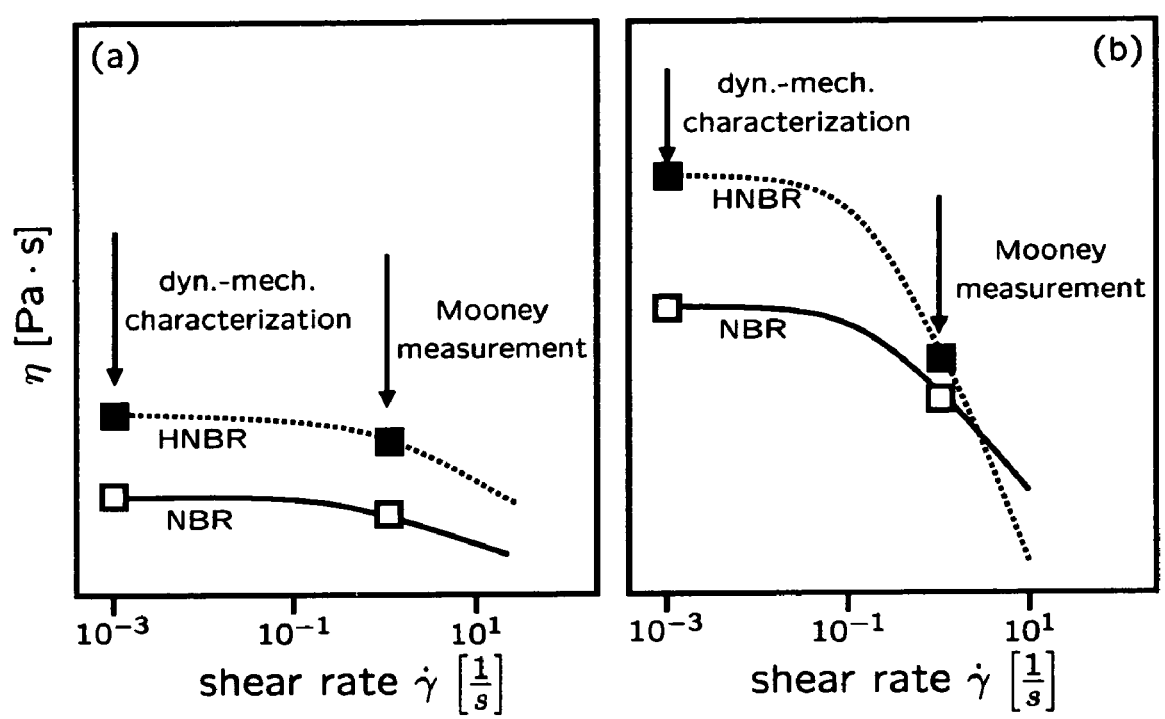
FIG. 16 shows the influence of the shear rate on the viscosity for polymers with linear (a) and long-chain branched chain architecture for polymers with different chain lengths and architecture. The fraction of the long-chain-branched chains gives rise to a higher volume viscosity at low shear rates (compare solid curves in FIGS. 16 (a) and 16 (b).

A schematic diagram of this behaviour is shown in FIG. 16 (influence of the shear rate on the viscosity for polymers with linear (a) and long-chain-branched chain architecture) for polymers with different chain lengths and architecture. FIG. 16a shows the behaviour of a linear NBR (solid curve). The hydrogenation of the NBR increases the flexibility and consequently the viscosity (see dotted curve). The ratio between the viscosities of the HNBR and of the NBR at low and high shear rates is virtually constant, since the influence of the shear rate on the viscosity is comparatively low for linear polymer chains.

This changes drastically when an NBR with a fraction of long-chain-branched chains is considered (see FIG. 16b). The fraction of the long-chain-branched chains gives rise to a higher volume viscosity at low shear rates (compare solid curves in FIGS. 16a and 16b). The stronger influence of the hydrogenation on the viscosity of the branched structures gives rise to a higher viscosity of the HNBR at low shear rates (see dotted curve in FIG. 16b). The ratio between the viscosities of HNBR and NBR at small amplitudes is therefore significantly higher than the viscosity ratio of linear chains.

Since the influence of the shear rate on the viscosity for branched chains is clearer, the viscosity of a branched chain is less than the viscosity of a linear chain at the limit of high shear rates. A branched structure in the polymer therefore gives rise to a smaller ratio between the viscosities of HNBR and NBR at relatively high shear rates (compare viscosities in FIGS. 16a and 16b at a shear rate of $\dot\gamma \approx 10^{-3}$ [1/s]), than a linear polymer with comparable molar mass.

The results of the NR and NBR/HNBR measurements show that the DMA (i.e. the process performed according to the present invention) provides a novel process for the characterization of the molar mass and its distribution. The advantage of DMA over GPC becomes obvious when polymer chains with relatively high molar mass or fractions of long-chain-branched structures are present.

Since the DMA has not been performed with calibration, the results cannot be used for a quantitative determination of the molar mass. A rough estimate of the molar masses has, however, been achieved by a comparison of the DMA and GPC results. This is shown in FIGS. 9, 10 and 11, in which peak values of the molar masses from GPC and DMA measurements have been used as the basis for comparison.

The calibration of the GPC is commonly performed with a series of polystyrene (or polyisoprene) samples with varying molar mass and narrow molar mass distribution. Generally, the molar mass of an unknown polymer is calculated on the basis of the polystyrene calibration. When the polymer-solvent interaction or the chain flexibility of a characterized polymer is different from polystyrene (or polyisoprene), a systematic deviation in the molar mass occurs. The GPC measurements then give rise only to a qualitative result for the molar mass and its distribution.

A calibration of the DMA can, if required, be performed similarly to the GPC process. The comparison of the calibration with different polymers (for example polystyrene and polyisoprene) would not only enable a quantitative characterization of their molar masses but additionally provide direct information about their chain flexibility.

What is claimed is:

1. Process for determining a molecular weight distribution in a polymer, comprising measuring a complex shear modulus as a function of the frequency, fitting an analytical function to the measured complex shear modulus or to a mastercurve determined from the measured complex shear modulus, and calculating the molecular weight distribution therefrom, wherein a sum of at least three Cole-Cole functions according to $$F^*_{CCV}(f) = \sum_{v=0}^{\frac{n}{4}} F_{0_v} \frac{\sqrt{\iota \frac{f}{f_{0_v}}}}{1 + \sqrt{\iota \frac{f}{f_{0_v}}}}$$

is selected as the analytical function, wherein the width parameter selected in the Cole-Cole functions is b=0.5, wherein the relaxation time spectrum is calculated proceeding therefrom, where the parameters $F_{0_v}$ and $f_{0_v}$ are selected so as to give rise to the sum of the Cole-Cole functions in log-log plot, wherein the real part has the slope of 2 in the limiting case of small frequencies and an imaginary part has the slope of 1 in the limiting case of small frequencies.

2. Process according to claim 1, wherein the relaxation time spectrum is determined from the analytical function and the molecular weight distribution is calculated with the relaxation time spectrum and the generalized mixing rule.

3. Process according to claim 1, wherein the complex shear modulus is measured at different temperatures and a mastercurve is curved from the measured values.

4. Process according to claim 1, wherein the generalized mixing rule $$w(m) = \frac{1}{\beta}\left(\frac{\alpha}{G_0}\right)^{\frac{1}{\beta}} h(m) \left[\int_{lnm}^{\infty} h(m') d\ln m'\right]^{\frac{1}{\beta}-1}$$

is used to determine the molecular weight distribution.

5. Process according to claim 1, wherein a relaxation time spectrum is corrected by the segment relaxations of a glass process.

6. The process according to claim 1, wherein the calculated molecular weight distribution covers a viscous flow state of the polymer.

7. The process according to claim 1, wherein a sum of five Cole-Cole functions, the following relationship exists between $F_{0_v}$ and $f_{0_v}$:

$$f_{0_0} = f_0 \quad f_{0_1} = \frac{f_0}{\sqrt{\Delta}} \quad f_{0_2} = \frac{f_0}{\Delta} \quad f_{0_3} = \sqrt{\Delta} \cdot f_0 \quad f_{0_4} = \Delta \cdot f_0$$

$$F_{0_1} = F_{0_3} = F_0 \cdot \Delta^{\frac{1}{4}} \cdot \frac{(\Delta^2 - 1) \cdot (\Delta - 1)}{\Delta^{\frac{7}{2}} - \Delta^2 - \Delta^{\frac{3}{2}} + 1}$$

$$F_{0_2} = F_{0_4} = F_0 \cdot \Delta \cdot \frac{(\Delta - 1) \cdot \left(\Delta^{\frac{1}{2}} - 1\right)}{\Delta^{\frac{7}{2}} - \Delta^2 - \Delta^{\frac{3}{2}} + 1}.$$

8. Process for determining a molecular weight distribution in a polymer, comprising measuring a complex shear modulus as a function of the frequency, fitting an analytical function to the measured complex shear modulus or to a mastercurve determined from the measured complex shear modulus, and calculating the molecular weight distribution there from, wherein the analytical function is a sum of Cole-Cole functions which is fitted to the measured complex shear modulus or to the mastercurve determined from the measured complex shear modulus, and wherein a sum of at least three Cole-Cole functions according to $$F^*_{CCV}(f) = \sum_{v=0}^{\frac{n}{4}} F_{0_v} \frac{\sqrt{\iota \frac{f}{f_{0_v}}}}{1 + \sqrt{\iota \frac{f}{f_{0_v}}}}$$

is fitted analytically to the complex shear modulus which has been measured as a function of frequency and is present in numeric form or to a mastercurve present in numerical form, and the relaxation time spectrum is calculated proceeding therefrom, where the parameters $F_{0_v}$ and $f_{0_v}$ are selected so as to give rise to the sum of the Cole-Cole functions in a log-log plot wherein a real part has the slope of 2 in the limiting case of small frequencies and an imaginary part has the slope of 1 in the limiting case of small frequencies.

* * * * *